US010166090B2

(12) United States Patent
Nowak et al.

(10) Patent No.: US 10,166,090 B2
(45) Date of Patent: Jan. 1, 2019

(54) DEVICE FOR DETECTING THE THREE-DIMENSIONAL GEOMETRY OF OBJECTS AND METHOD FOR THE OPERATION THEREOF

(71) Applicant: a.tron3d GmbH, Klagenfurt am Worthersee (AT)

(72) Inventors: Christoph Nowak, Vienna (AT); Horst Koinig, Klagenfurt (AT); Jurgen Jesenko, Finkenstein (AT)

(73) Assignee: A.TRON3D GMBH, Klagenfurt am Worthersee (AT)

( * ) Notice: Subject to any disclaimer, the term of this patent is extended or adjusted under 35 U.S.C. 154(b) by 155 days.

(21) Appl. No.: 15/176,206

(22) Filed: Jun. 8, 2016

(65) Prior Publication Data

US 2016/0287358 A1  Oct. 6, 2016

Related U.S. Application Data

(62) Division of application No. 14/377,030, filed as application No. PCT/AT2013/000018 on Feb. 4, 2013, now Pat. No. 9,861,456.

(30) Foreign Application Priority Data

Feb. 6, 2012 (DE) ........................ 10 2012 100 953

(51) Int. Cl.
*A61C 9/00* (2006.01)
*H04N 13/189* (2018.01)
(Continued)

(52) U.S. Cl.
CPC ............ *A61C 9/006* (2013.01); *A61B 5/1076* (2013.01); *A61B 5/1077* (2013.01);
(Continued)

(58) Field of Classification Search
CPC ..... A61C 9/006; A61B 5/1076; A61B 5/1077; A61B 5/1079; A61B 5/4547;
(Continued)

(56) References Cited

U.S. PATENT DOCUMENTS

| 4,837,732 A | 6/1989 | Brandestini et al. |
| 5,661,519 A * | 8/1997 | Franetzki ........... A61B 1/00183 348/65 |

(Continued)

FOREIGN PATENT DOCUMENTS

| AT | 508563 | 2/2011 |
| DE | 19636354 | 3/1998 |

(Continued)

OTHER PUBLICATIONS

International Search Report, dated Jun. 20, 2013, from corresponding PCT application.

(Continued)

*Primary Examiner* — Nicholas Lucchesi
(74) *Attorney, Agent, or Firm* — Young & Thompson

(57) ABSTRACT

The invention relates to a device for detecting the three-dimensional geometry of objects, in particular teeth, comprising a handpiece which is provided with at least one position sensor for detecting the change of the spatial position of the handpiece, and an optical device having at least one camera for capturing images and at least one light source for at least one projector. The position sensor in the handpiece initially determines the size of the change of the spatial position of the device. It is determined therefrom, how many pictures the camera can take in a defined time unit.

18 Claims, 2 Drawing Sheets

(51) Int. Cl.

| | |
|---|---|
| *H04N 13/194* | (2018.01) |
| *H04N 13/254* | (2018.01) |
| *A61B 5/107* | (2006.01) |
| *G01B 21/04* | (2006.01) |
| *G01B 11/25* | (2006.01) |
| *A61B 5/00* | (2006.01) |
| *G01B 11/02* | (2006.01) |
| *G06T 7/00* | (2017.01) |
| *H04N 7/18* | (2006.01) |
| *H04N 13/221* | (2018.01) |

(52) U.S. Cl.
CPC .......... *A61B 5/1079* (2013.01); *A61B 5/4547* (2013.01); *G01B 11/022* (2013.01); *G01B 11/2513* (2013.01); *G01B 21/042* (2013.01); *G06T 7/0012* (2013.01); *H04N 7/18* (2013.01); *H04N 13/189* (2018.05); *H04N 13/194* (2018.05); *H04N 13/221* (2018.05); *H04N 13/254* (2018.05); *A61B 2560/0209* (2013.01); *H04N 2213/001* (2013.01)

(58) Field of Classification Search
CPC .............. G01B 11/022; G01B 11/2513; G01B 21/042; G01B 7/0012; H04N 7/18; H04N 13/0221; H04N 13/0253
See application file for complete search history.

(56) References Cited

U.S. PATENT DOCUMENTS

| | | | | |
|---|---|---|---|---|
| 8,520,925 | B2* | 8/2013 | Duret | A61B 1/24 |
| | | | | 382/100 |
| 9,138,319 | B2* | 9/2015 | Fanson | A61F 2/46 |
| 9,202,385 | B2* | 12/2015 | Pabst | G09B 9/003 |
| 9,247,998 | B2* | 2/2016 | Hladio | A61B 5/4571 |
| 9,314,188 | B2* | 4/2016 | Hladio | A61B 5/1072 |
| 9,454,846 | B2* | 9/2016 | Pesach | A61C 9/0033 |
| 9,683,837 | B2* | 6/2017 | Siercks | G01B 11/2513 |
| 9,808,148 | B2* | 11/2017 | Miller | A61B 1/0684 |
| 2003/0164952 | A1 | 9/2003 | Deichmann et al. | |
| 2004/0218792 | A1* | 11/2004 | Spoonhower | A61B 5/0084 |
| | | | | 382/128 |
| 2005/0090749 | A1 | 4/2005 | Rubbert | |
| 2009/0087050 | A1* | 4/2009 | Gandyra | G01B 11/03 |
| | | | | 382/128 |
| 2010/0239136 | A1* | 9/2010 | Gandyra | G01B 11/03 |
| | | | | 382/128 |
| 2010/0284589 | A1 | 11/2010 | Thiel et al. | |
| 2011/0242281 | A1 | 10/2011 | Schmidt | |
| 2012/0218389 | A1 | 8/2012 | Nowak et al. | |
| 2014/0071258 | A1 | 3/2014 | Gandyra | |

FOREIGN PATENT DOCUMENTS

| | | |
|---|---|---|
| DE | 102007060263 | 2/2009 |
| EP | 0250993 | 1/1988 |
| EP | 0837659 B1 | 11/1999 |
| EP | 2166303 | 3/2010 |
| WO | 2009063088 | 5/2009 |
| WO | 2010012838 | 2/2010 |

OTHER PUBLICATIONS

European Office Action for Application No. 13708647, dated Aug. 13, 2018, with partial English translation provided.

* cited by examiner

DEVICE FOR DETECTING THE THREE-DIMENSIONAL GEOMETRY OF OBJECTS AND METHOD FOR THE OPERATION THEREOF

The invention relates to a device for detecting the three-dimensional geometry of objects, especially teeth, with a handpiece that has an optical apparatus with at least one camera and with at least one light source.

The invention furthermore relates to a method for operating a device for detecting the three-dimensional geometry of objects, especially teeth, with a handpiece that has at least one position sensor for detecting the change of the spatial position of the handpiece and an optical apparatus with at least one camera for taking pictures and with at least one light source for a projector.

A device of the initially-mentioned type is known from, for example, AT 508 563 B. In this case, the area of application of the invention extends to the recording of digital tooth and jaw impressions, assistance in diagnosis, supervision of tooth treatments, and reliable monitoring of inserted implants. In addition to further applications in the field of medical and industrial technology, for example in the field of endoscopy, objects that are poorly accessible can also be stereometrically measured.

The use of a position sensor is known from, for example, U.S. Pat. No. 5,661,519 A.

The object of the invention is to improve these devices such that they can be operated with a power supply that is as small as possible. Thus, operation by means of an energy storage mechanism that is housed in the handpiece itself and that is therefore small will be made possible.

In a device of the initially-mentioned type, this object is achieved in that the optical apparatus has exclusively rigidly attached parts and in that there is a means for producing light of the light source in the handpiece.

This object is achieved in a method of the initially-mentioned type in that it is determined—by the position sensor in the handpiece—how high a change in the spatial position of the device is, and from that it is determined how many pictures are taken by the camera within a defined unit of time.

By placing the means for generating light directly in the handpiece, long optical paths, for example over fiber optic cables or many deflection mirrors, are avoided. In this case, a differentiation is made between the light source, therefore everything that can emit light, for example the end of a fiber optic cable, and the means for producing light, for example a laser or the semiconductor of an LED.

By abandoning long optical paths, a means for producing light with lower output can be used in order to sufficiently illuminate the object. This means a notable energy savings.

The rigid mounting of all elements of the optical apparatus means that it is not possible to focus the optics of the camera. All calibrations of the optical apparatus therefore take place in the preliminary area. Here, it is especially important to achieve an optimum setting of the aperture. In this case, a smaller aperture is good for a larger depth of field; for a larger aperture, less illumination is required for a relatively good picture.

In one especially preferred embodiment, the device has an apparatus for synchronizing the power supply of the light source and the camera. Thus, the camera and light source are synchronously operated according to one preferred embodiment of the method. Large outputs with a comparatively small energy expenditure can be achieved by pulsing of light at spots. In this embodiment of the invention, the power supply is also interrupted on the sides of the picture. Thus, unilluminated pictures are avoided, and additional energy is saved.

In a further preferred embodiment, the handpiece has at least one position sensor, especially an acceleration sensor, a magnetic field sensor and/or a tilt sensor. With the latter, it is determined according to the method how large the change in the spatial position of the device is, and it is ascertained therefrom how many pictures are to be taken by the camera within one defined unit of time. In this way, taking more images of the same site with less motion than is necessary for optimum detection of the geometry can be avoided.

In this sense, in one preferred implementation, the image rate of images taken can be changed; preferably, the image rate is between 1 and 30 images per second.

In addition or alternatively, according to one preferred implementation of the method, the image rate can also be adapted depending on whether a higher or lower charging state of an energy storage mechanism or a higher or lower possible discharge current is available. Thus, for a higher charging state or discharge current, more light pulses can be emitted and received than at a lower charging state or discharge current.

In one possible embodiment of the invention, it can be additionally determined how many images of a defined region have been taken. From this value, a quality can be assigned to a recorded region of the object and can optionally be reproduced in the 3D display of the geometry of the object so that the user can react to it. Regions from which only a few data have been acquired and that therefore have a greater risk of deviations from the geometry of the object can be displayed in red, for example. Regions in which the number of pictures is already at a value that is sufficient for the desired quality can be displayed in green, for example. Other colors for the intermediate stages are likewise conceivable as for regions in which an optimum value has already been achieved; therefore, further pictures no longer entail a significant improvement of the acquired data. Of course, only regions that have poorer quality can also be colored.

For the purpose of saving energy, according to an additional or alternative process step for a defined region, it can be determined how many pictures of this region have already been taken and, upon reaching a defined number of pictures, no further pictures of this region are taken. This measure is, moreover, suitable for optimizing the required processing steps in a computer unit that processes the recorded data or for saving computing power that is required.

In one preferred embodiment, the optical apparatus has at least one projector for projection of patterns. The projection of patterns improves the possibilities for detecting the three-dimensional geometry.

In another preferred embodiment, the field angle of the camera and the field angle of the projector overlap one another at least 50%, preferably at least 80%, and especially preferably at least 90%. The field angle is the conical region in which the projection or picture-taking occurs. A proportion of the expended energy that is as large as possible is used due to the overlapping that is as large as possible.

In one preferred embodiment, the device has an electrical energy storage mechanism that can optionally be recharged. The latter can be used as the sole energy source of the device. In this case, it is useful if the device furthermore has a data storage mechanism or a possibility of wireless data transmission. Thus, the device can be moved completely freely without a cable. In one embodiment in which the data are stored, it is appropriate to link the later transmission of data, for example via a USB connection, to the charging of the energy storage mechanism.

There is preferably an opening that can be hygienically or tightly sealed in the housing for replacement of the energy storage mechanism. Thus, for example, an operator after use of the scanner can replace the at least partially exhausted energy storage mechanism by a fully charged one. Alternatively or additionally, a skilled worker can also replace the energy storage mechanism after a certain number of charging cycles and an actual or expected decline of the output of the energy storage mechanism.

Alternatively or additionally, in a further preferred implementation of the invention, it can be ascertained from the determined value of the available charge whether the device is to be operated optionally with two or three or more cameras. Thus, different operating modes are formed for different outputs of the power supply or for different charging states.

In one especially preferred implementation of the method, the data that have been acquired by the camera are relayed to a computer unit or a storage medium without further processing or conditioning. Thus, the energy expenditure that otherwise for a processor or chip that conventionally carries out this processing or conditioning is completely avoided. The further processing in the computer unit can take place at least in part in the GPU; however, it has been shown that it is useful especially with respect to the speed of data processing to process in the GPU a part of the data acquired for detection or computation of the three-dimensional geometry. Thus, it is possible to convert the data, especially two-dimensional images that have been taken by means of the camera, without noteworthy loss of time, directly into a three-dimensional representation on a display or into a data file that is available on a storage medium (for example, a 3D file in STL format).

The device can have a thermovoltaic element according to one preferred embodiment. With this element, according to one preferred embodiment of the method, electrical energy can be obtained from the heat that arises during operation. This energy can be used, on the one hand, directly for operating the device; on the other hand, however, especially when the device is cooled, an energy storage mechanism can also be supplied with the energy obtained.

Other preferred embodiments and implementations of the invention are the subject matter of the other dependent claims.

The invention is further explained below with reference to the drawings.

Figure 1:
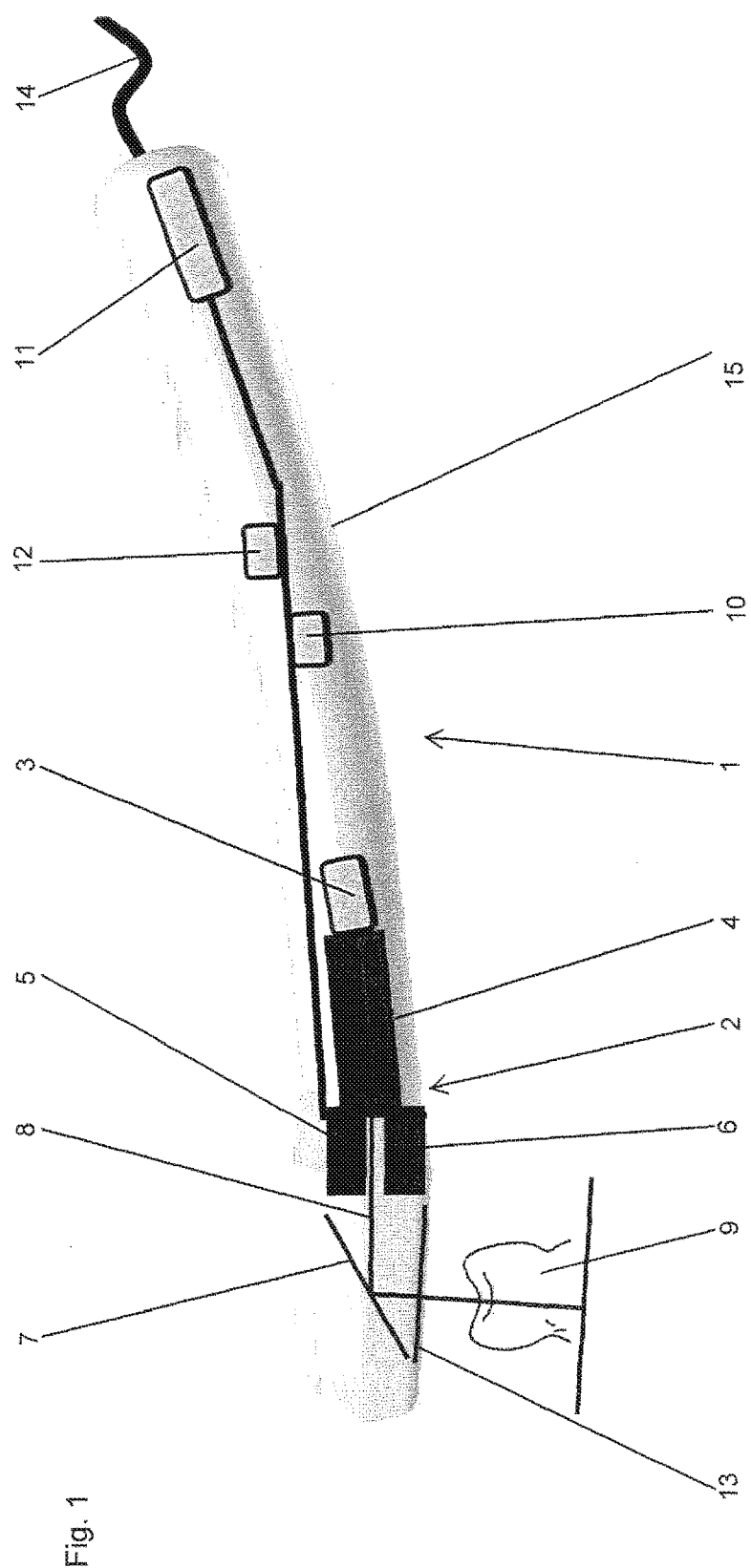
FIG. 1 shows a schematic representation of one embodiment of the invention.

FIG. 1 shows one exemplary embodiment of the device, consisting of a handpiece 1, in which there is an optical apparatus 2 that contains a light source 3, a projector 4, a first camera 5, a second camera 6, and a mirror 7. In front of the mirror in the housing 15 of the handpiece 1, there is a recess. The latter is provided with a transparent cover 13 for hygienic reasons and for protection of the components that are located in the handpiece 1.

In this embodiment, the light source 3 is an LED. In this embodiment, therefore, a means for producing the light (not shown in the drawings) is located in the form of a semiconductor directly in the light source 3. The further path of the light inside and outside of the device is shown by an exemplary light beam 8.

In this case, this beam first travels through the projector 4. Here, the projector 4 is used for projection of patterns onto the object. In this case, depending on the type of detection of the geometry, it can be both regular patterns, such as, for example, stripes, and irregular patterns, such as, for example, irregular point patterns.

Downstream from the projector 4, the light beam 8 is incident on the mirror 7 and is deflected via the mirror onto the object 9, whose geometry is to be detected. In the depicted embodiment, the object 9 is a tooth. In an embodiment that is not shown in the drawings and in which the light source 3 and the projector 4 are already aligned in the direction of the object, the mirror 7 can also be omitted.

The cameras 5, 6 record the pattern that has been projected onto the tooth 9 and from which later the geometry of the tooth 9 is computed. According to one preferred implementation, all computations in this respect take place in a computer unit that is located outside the handpiece 1, as a result of which the power consumption of internal chip sets or processors is minimized. The device can be connected to this computer unit both physically using a cable 14 and also wirelessly. In the embodiment, there is a wireless connection (for example, Bluetooth or WLAN). For this purpose, in the handpiece there is a means for wireless data transmission 10, especially a transmitter and optionally a receiver. The depicted cable 14 is therefore not connected during actual operation, but at a low charging state of the energy storage mechanism can be connected, for example, as auxiliary current.

Furthermore, in the handpiece 1, there is an energy storage mechanism 11 that can be optionally recharged. Consequently, a cable on the handpiece 1 can be completely omitted, as a result of which there is optimum freedom of motion.

The drawings, moreover, show a position sensor 12. With the latter, it can be determined how large the spatial motion of the handpiece 1 is. For this purpose, the position sensor 12 can be, for example, an acceleration sensor, a terrestrial magnetic field sensor or a tilt sensor. In this case, combinations of different sensor types increase the accuracy with which the change in the spatial position or the movement of the handpiece 1 is determined.

Figure 2:
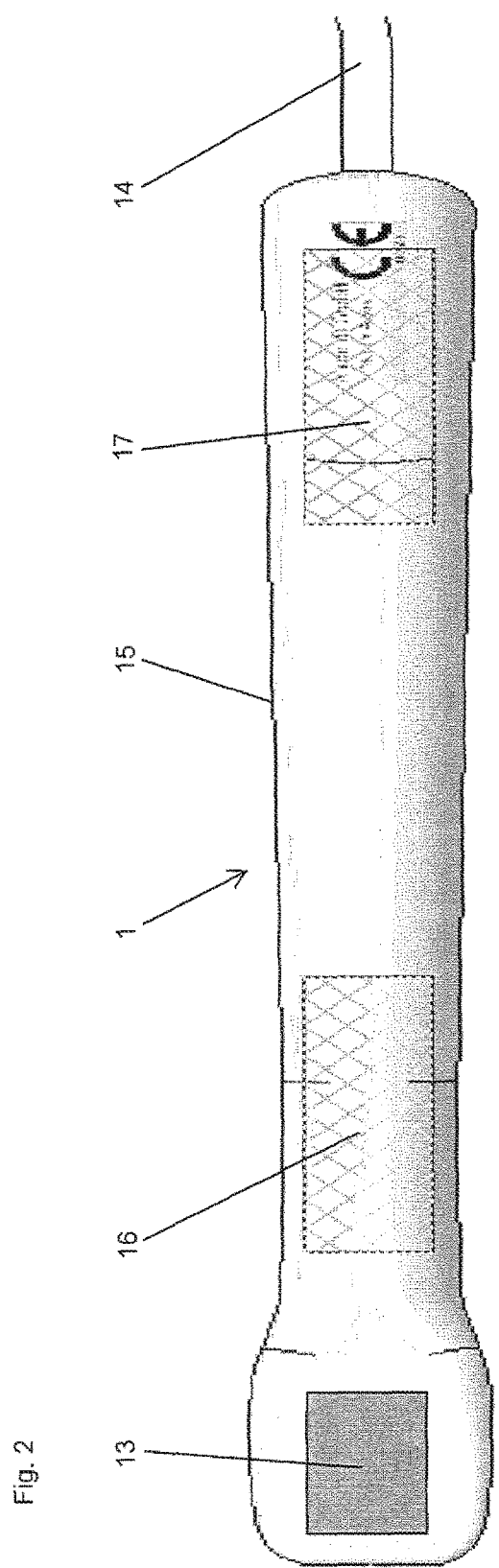
FIG. 2 shows a schematic view of the bottom of one embodiment of the invention.

FIG. 2 shows a schematic view of the bottom of one embodiment of the invention. Here, two regions 16, 17 are shown in which a thermovoltaic element could be placed.

In the first region 16, the thermovoltaic element is located directly on the bottom, therefore the side on which the covering 13 is located, in the vicinity of the optical apparatus 2. This is advantageous since the optical apparatus 2, especially the projector 4, produces mostly heat during operation and the heat can be used with losses that are as low as possible.

If the thermovoltaic element is placed in the second region 17, this has the advantage that it can be dimensioned to be larger; however, a heat conductor that conducts the heat from the optical apparatus 2 to the thermovoltaic element is then necessary. Also, in a positioning of the thermovoltaic element in the second region 17, attachment to the bottom of the handpiece 1 is useful, so that one side of the thermovoltaic element that releases heat and that points to the outside according to one preferred embodiment of the invention is not covered by the hand of the user.

The invention claimed is:

1. Method for operating a device for detecting the three-dimensional geometry of objects, especially teeth, the device comprising a handpiece that has at least one position sensor for detecting the change in the spatial position of the handpiece and an optical apparatus comprising at least one camera for taking images and at least one light source for at least one projector, comprising determining by the position sensor in the handpiece how large a change in the spatial position of the device is, and then determining how many images are taken by the camera within a defined period of time.

2. Method according to claim 1, wherein the camera is operated synchronously to the light source of the projector.

3. Method according to claim 2, wherein the data that have been acquired by the camera are relayed to a computer unit or a storage medium without further processing or conditioning.

4. Method according to claim 2, wherein an image rate of the images taken is between 1 and 30 images per second.

5. Method according to claim 2, wherein for a defined surface region of the object, it is determined how many images of this region have already been taken, and wherein starting with reaching a defined number of images, no further images of this region are taken.

6. Method according to claim 2, wherein electrical energy is obtained from heat that arises during the operation of the device, via a thermovoltaic element.

7. Method according to claim 1, wherein the data that have been acquired by the camera are relayed to a computer unit or a storage medium without further processing or conditioning.

8. Method according to claim 7, wherein an image rate of the images taken is between 1 and 30 images per second.

9. Method according to claim 7, wherein for a defined surface region of the object, it is determined how many images of this region have already been taken, and wherein starting with reaching a defined number of images, no further images of this region are taken.

10. Method according to claim 7, wherein electrical energy is obtained from heat that arises during the operation of the device, via a thermovoltaic element.

11. Method according to claim 1, wherein an image rate of the images taken is between 1 and 30 images per second.

12. Method according to claim 11, wherein for a defined surface region of the object, it is determined how many images of this region have already been taken, and wherein starting with reaching a defined number of images, no further images of this region are taken.

13. Method according to claim 11, wherein electrical energy is obtained from heat that arises during the operation of the device, via a thermovoltaic element.

14. Method according to claim 1, wherein for a defined surface region of an object, it is determined how many pictures of this region have already been taken, and wherein starting with reaching a defined number of pictures, no further pictures of this region are taken.

15. Method according to claim 14, wherein electrical energy is obtained from heat that arises during the operation of the device, via a thermovoltaic element.

16. Method according to claim 1, wherein electrical energy is obtained from heat that arises during the operation of the device, via a thermovoltaic element.

17. Method according to claim 16, wherein the energy that has been obtained via the thermovoltaic element is used for operation of the device.

18. Method according to claim 16, wherein the energy that has been obtained via the thermovoltaic element is stored in an energy storage mechanism.

* * * * *